(12) United States Patent
Cai

(10) Patent No.: US 11,612,656 B2
(45) Date of Patent: Mar. 28, 2023

(54) USE OF SMALL MOLECULE BASED ON INDOTRICARBOCYANINE STRUCTURE IN PREPARATION OF MEDICINES FOR TUMOR PHOTOTHERMAL THERAPY

(71) Applicant: Nanjing Nuoyuan Medical Devices Co., LTD., Jiangsu (CN)

(72) Inventor: Huiming Cai, Jiangsu (CN)

(73) Assignee: Nanjing Nuoyuan Medical Devices Co., LTD., Nanjing (CN)

( * ) Notice: Subject to any disclaimer, the term of this patent is extended or adjusted under 35 U.S.C. 154(b) by 0 days.

(21) Appl. No.: 17/828,255

(22) Filed: May 31, 2022

(65) Prior Publication Data
US 2022/0387591 A1    Dec. 8, 2022

(30) Foreign Application Priority Data
May 31, 2021 (CN) .......................... 202110598438.4

(51) Int. Cl.
*A61K 41/00* (2020.01)
*A61P 35/00* (2006.01)

(52) U.S. Cl.
CPC .......... *A61K 41/0052* (2013.01); *A61P 35/00* (2018.01)

(58) Field of Classification Search
None
See application file for complete search history.

(56) References Cited

PUBLICATIONS

RUTTGER et al., European Journal of Organic Chemistry (2019), pp. 4791-4796.*

* cited by examiner

*Primary Examiner* — Brian J Davis
(74) *Attorney, Agent, or Firm* — Casimir Jones, SC; Robert A. Goetz

(57) ABSTRACT

The present disclosure belongs to the field of medicines, and particularly relates to property researches of an indotricarbocyanine structure-based small molecule medicine for tumor photothermal therapy. The present disclosure is based on a large-conjugated water-soluble indotricarbocyanine dye compound developed by the applicant, and the compound can be used as a photothermal therapeutic agent, and has a potential development and application prospect. In the present disclosure, the compound is found to be an excellent tumor photothermal therapy medicine, and such use of this compound has not been found and reported at present. Through in-vitro property researches on the photothermal efficiency of this compound, a foundation is provided for clinical application of the indocyanine green-like small molecule photothermal therapeutic agent, and a basis is provided for researches of the small molecule photothermal therapeutic agent.

11 Claims, 8 Drawing Sheets

USE OF SMALL MOLECULE BASED ON INDOTRICARBOCYANINE STRUCTURE IN PREPARATION OF MEDICINES FOR TUMOR PHOTOTHERMAL THERAPY

CROSS-REFERENCE TO RELATED APPLICATION

The present disclosure claims the priority to the Chinese patent application with the filing No. 202110598438.4, filed on May 31, 2021 with the State Intellectual Property Office of China, and entitled "Use of Small Molecule Based on Indotricarbocyanine Structure in Preparation of Medicines for Tumor Photothermal Therapy", the contents of which are incorporated by reference herein in entirety.

TECHNICAL FIELD

The present disclosure belongs to the field of medicines, and particularly relates to property researches of indotricarbocyanine structure-based small molecule medicines for tumor photothermal therapy and a use of the indotricarbocyanine structure-based small molecule medicines in therapy.

BACKGROUND ART

Photothermal therapy is a novel therapeutic approach. It is well known that currently, the main therapeutic approaches in clinical practice are surgery, drug chemotherapy, and radiotherapy. Surgery can remove early solid tumors, but may result in incomplete resection, and leave cancer cells behind, thus causing metastasis and recurrence of cancer after surgery. Drug chemotherapy and radiotherapy are the two most commonly used treatment strategies. Although they have an inhibitory effect on tumors, the patients' adaptability is poor due to large toxic and side effects, drug tolerance, and inherent toxicity of radiation rays. Based on the drawbacks of the above treatment methods, the non-invasive photothermal therapy has received extensive attentions and researches due to its high specificity, short treatment time, significant effect, reduced damage to surrounding tissues, and good bioavailability.

Photothermal conversion materials are quite important for photothermal therapy. From the development process of photothermal therapy materials, the first-generation to third-generation photothermal materials are nano therapy platforms, including noble metal nanoparticles, carbon nanoparticles, and metal compound nanoparticles. However, the nanoparticle therapy platform has inherent defects such as a high cost, difficult degradation in organisms, and possibility of causing adverse reactions of organisms. As having the small size effect, surface effect, quantum scale effect, and macroscopic quantum tunneling effect which are not possessed by common particles, the nanoparticles show the thermal, optical, electrical, magnetic, catalytic and sensitive properties and so on different from those of conventional materials, and may cause special biological effect different from that of the common particles after entering ecological environment and organisms. Researches show that the nanoparticles can enter the organisms through various routes, such as respiratory tract, skin, and digestive tract, which not only can cause damage to various tissues and organs of animals, but also cause toxic effects on organisms at multiple levels, such as overall animal level, cellular level, subcellular level, and protein and gene level.

For example, researches find that the silver nanoparticles can cause obvious endoplasmic reticulum stress reaction of organs such as lungs, livers, and kidneys of animals, wherein significant apoptosis phenomenon occurs in the lungs and the kidneys. The titanium oxide nanoparticles orally infused can cause liver function impairments such as reduced total bilirubin, and globulin increase of male rats, and kidney function impairments such as significant increase of blood urea nitrogen and creatinine level.

For another example, in 2014, International Agency for Research on Cancer (IARC) identified a carbon nanotube named "MWCNT-7" to be "likely to be carcinogenic to humans". According to rodent experiments, the introduction of MWCNT-7 will cause peritoneal mesothelioma, and the injection of CNTs into peritoneum and scrotum of female rats will promote the formation of bronchoalveolar adenoma and carcinoma. Researches show that in vivo and in vitro genotoxicity is positive to the carbon nanotube; symptoms of pneumonia are observed in both rats and mice, into which carbon nanotubes are introduced, and a number of research reports have also further confirmed the carcinogenicity of carbon nanotubes. In 2019, the researches of Chinese scholars also proved that the accumulation of carbon nanotubes in the lungs will accelerate the metastasis of tumors. In addition, carbon nanotubes also exhibit reproduction toxicity. it was found through researches that intravenous injection of carbon nanotubes into pregnant mice will cause lethality and teratogenicity of mouse embryos. The ratios of early abortion and fetal malformations are also higher if the female mice are exposed to carbon nanotube environments.

In order to overcome the above drawbacks of nanoparticles, the fourth-generation organic small molecule dyes with photothermal conversion have been developed.

Indocyanine green (ICG), as a fluorescent tricarbocyanine dye, was developed by Kodak Research Laboratories in 1955, and started to be used for the diagnosis of human diseases since 1956. Most clinical applications of ICG utilize its fluorescent function. With the in-depth researches of ICG, researchers found that ICG has a certain photothermal conversion efficiency and can be developed for small molecule photothermal therapeutic agents. During 2012 to 2013, the Children's Cancer Center of Lebanon of the American University of Beirut Medical Center carried out ICG-enhanced pupillary photothermal therapy for three children suffering from bilateral retinoblastoma, and achieved a better therapeutic effect. However, researches show that at the light irradiation at a power density of 1 W/cm$^2$, free ICG of a concentration of 20 μg/ml has the photothermal conversion efficiency (PTCE) of 15.1%, and the photothermal conversion efficiency still needs to be improved.

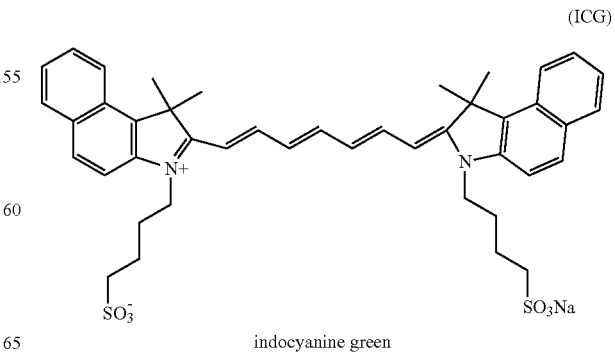

(ICG)

indocyanine green

Based on the problems found above, the present disclosure discloses photothermal use of a small molecule compound ICG-II based on an indotricarbocyanine structure. This compound structure is based on a large-conjugated water-soluble indotricarbocyanine dye compound. This compound can be used as a photothermal therapeutic agent, and has a potential development and application prospect. The present disclosure discloses that this compound is an excellent tumor photothermal therapy medicine, and such use has not been found and reported at present. Through in-vitro property researches on the photothermal efficiency of this compound, a foundation is provided for clinical application of the indocyanine green-like small molecule photothermal therapeutic agent, and a basis is provided for researches of the small molecule photothermal therapeutic agent.

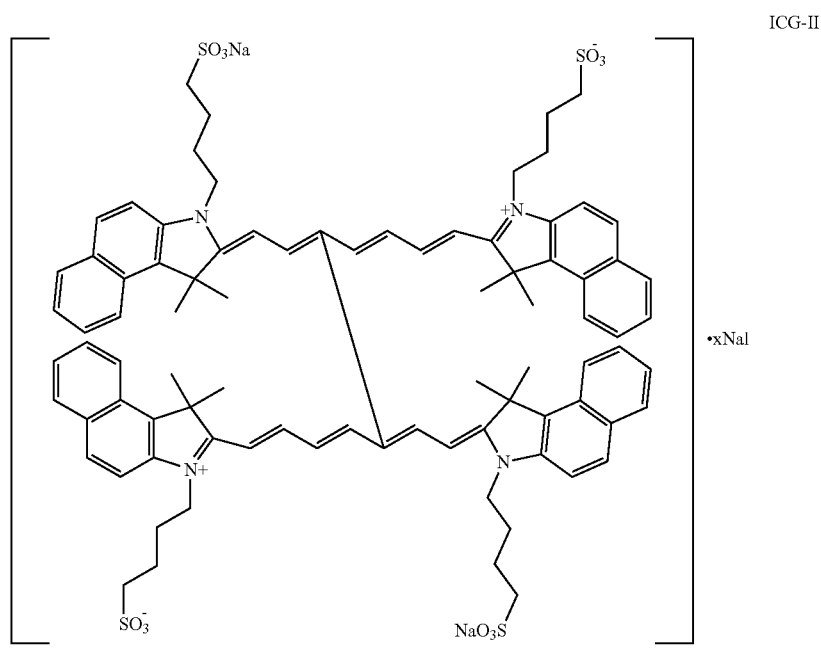

In the above, x is greater than or equal to 1.

SUMMARY

An objective of the present disclosure includes providing a tumor photothermal therapy medicine, use of a small molecule based on an indotricarbocyanine structure in preparation of a tumor photothermal therapy medicine, and an efficient method for tumor photothermal therapy.

The present disclosure is realized as follows.

In a first aspect, the present disclosure provides a use of a small molecule based on an indotricarbocyanine structure in preparation of a tumor photothermal therapy medicine, wherein the small molecule in the indotricarbocyanine structure has the following structural formula:

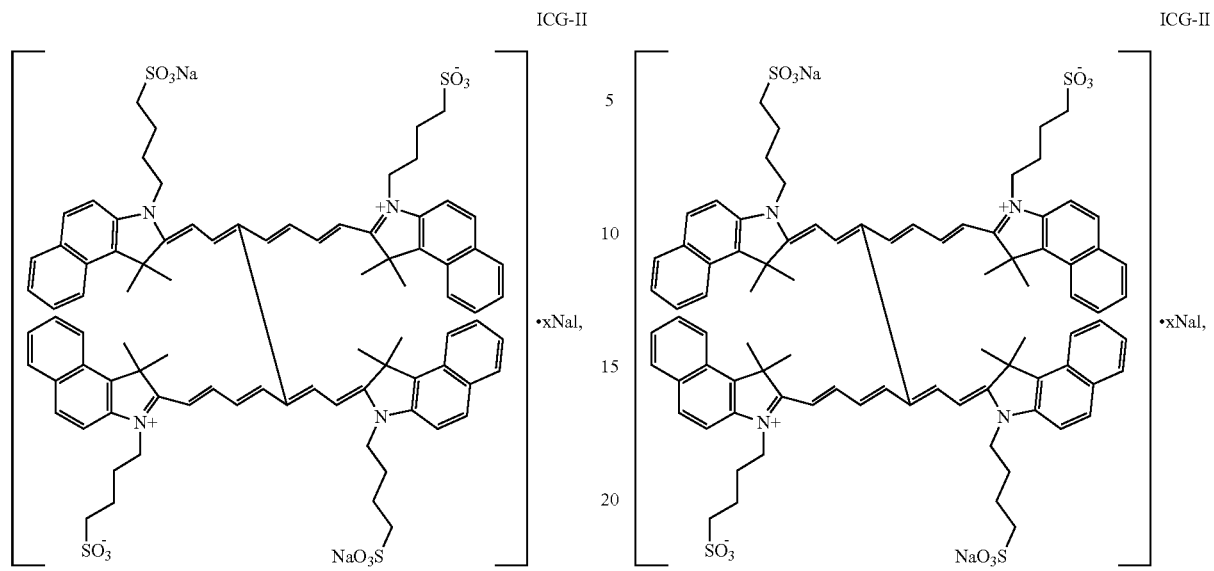

where x is greater than or equal to 1.

In an optional embodiment, the tumor photothermal therapy includes performing light irradiation on a to-be-treated area of a subject at a power density.

In an optional embodiment, the power density is 1.0-2.5 W/cm$^2$.

In an optional embodiment, the power density is 1.0 W/cm$^2$, 1.5 W/cm$^2$, 2.0 W/cm$^2$ or 2.5 W/cm$^2$.

In an optional embodiment, a wavelength of the light irradiation is 785 nm.

In an optional embodiment, the tumor is selected from the group consisting of liver cancer, retinoblastoma, lung cancer, leukemia, melanoma, pancreatic cancer, breast cancer, prostate cancer, ovarian cancer, bile duct cancer, bladder cancer, bone cancer, cervical cancer, colorectal cancer, esophageal cancer, gastric cancer, kidney cancer, laryngeal cancer, lymphoma, oral cancer, skin cancer, and thyroid cancer.

In a second aspect, the present disclosure provides a method for photothermally treating a tumor, including injecting a therapeutically effective amount of a photothermal reagent to a to-be-treated area of a subject, and performing light irradiation on the to-be-treated area of the subject with a laser device at a power density, wherein the photothermal reagent is a small molecule based on an indotricarbocyanine structure, wherein the small molecule of the indotricarbocyanine structure has a structural formula as follows:

where x is greater than or equal to 1.

In an optional embodiment, the power density is 1.0-2.5 W/cm$^2$.

In an optional embodiment, the power density is 1.0 W/cm$^2$, 1.5 W/cm$^2$, 2.0 W/cm$^2$ or 2.5 W/cm$^2$.

In an optional embodiment, a wavelength of the light irradiation is 785 nm.

In an optional embodiment, the tumor is selected from the group consisting of liver cancer, retinoblastoma, lung cancer, leukemia, melanoma, pancreatic cancer, breast cancer, prostate cancer, ovarian cancer, bile duct cancer, bladder cancer, bone cancer, cervical cancer, colorectal cancer, esophageal cancer, gastric cancer, kidney cancer, laryngeal cancer, lymphoma, oral cancer, skin cancer, and thyroid cancer.

In a third aspect, the present disclosure provides a small molecule compound based on an indotricarbocyanine structure for tumor photothermal therapy, wherein the small molecule of the indotricarbocyanine structure has a structural formula as follows:

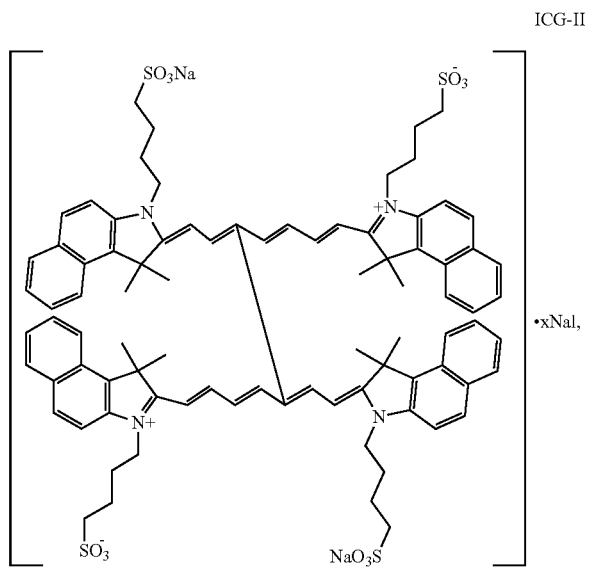

ICG-II where x is greater than or equal to 1.

In an optional embodiment, the tumor photothermal therapy includes performing light irradiation on a to-be-treated area of a subject at a power density.

In an optional embodiment, the power density is 1.0-2.5 W/cm².

In an optional embodiment, the power density is 1.0 W/cm², 1.5 W/cm², 2.0 W/cm² or 2.5 W/cm².

In an optional embodiment, a wavelength of the light irradiation is 785 nm.

In an optional embodiment, the tumor is selected from the group consisting of liver cancer, retinoblastoma, lung cancer, leukemia, melanoma, pancreatic cancer, breast cancer, prostate cancer, ovarian cancer, bile duct cancer, bladder cancer, bone cancer, cervical cancer, colorectal cancer, esophageal cancer, gastric cancer, kidney cancer, laryngeal cancer, lymphoma, oral cancer, skin cancer, and thyroid cancer.

Compared with the prior art, the technical solution of the present disclosure has the following beneficial technical effects.

The present disclosure finds for the first time the photothermal use of the small molecule compound ICG-II based on an indotricarbocyanine structure. Compared with the indotricarbocyanine photothermal reagents in the prior art, the brand new small molecule compound ICG-II based on an indotricarbocyanine structure provided in the present disclosure has a significantly improved photothermal conversion efficiency, and the photothermal conversion efficiency can be up to 75%.

The present disclosure provides a small molecule probe based on an indotricarbocyanine structure, efficient for tumor photothermal therapy. This small molecule probe has significant anti-tumor activity selective to light irradiation, and shows the properties of high activity and low toxic and side effects.

The small molecule probe based on an indotricarbocyanine structure provided in the present disclosure has excellent water solubility, has a high photothermal conversion efficiency in a small molecule state, does not need to be prepared into a nano material, avoids the defects of high biotoxicity and poor biological metabolism of nano materials, and has a wide clinical application prospect.

BRIEF DESCRIPTION OF DRAWINGS

In order to more clearly illustrate technical solutions of examples of the present disclosure, accompanying drawings which need to be used in the examples will be introduced briefly below, and it should be understood that the accompanying drawings below merely show some examples of the present disclosure, therefore, they should not be considered as limitation on the scope, and those ordinarily skilled in the art still could obtain other relevant accompanying drawings according to these accompanying drawings, without using any creative efforts.

DETAILED DESCRIPTION OF EMBODIMENTS

Figure 1:
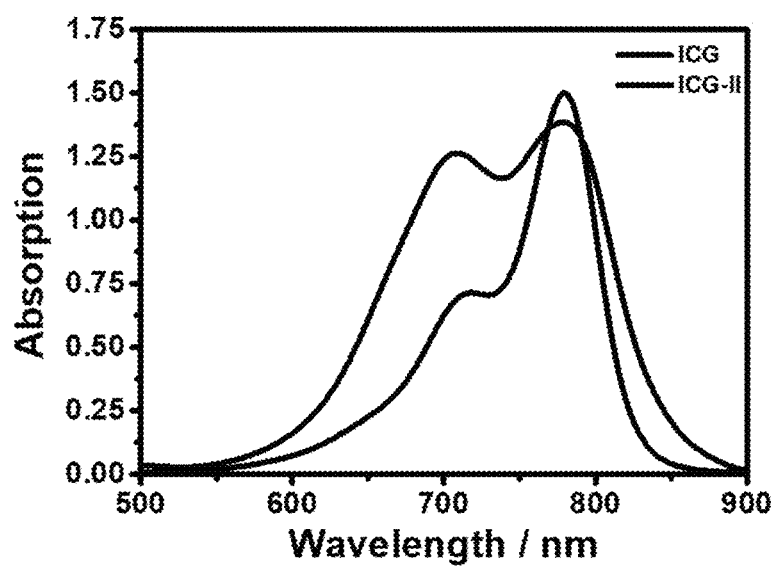
FIG. 1 shows ultraviolet absorption spectra of a tumor photothermal therapy medicine ICG-II in the present disclosure and an ICG, of a concentration of 10 PM.
Figure 2:
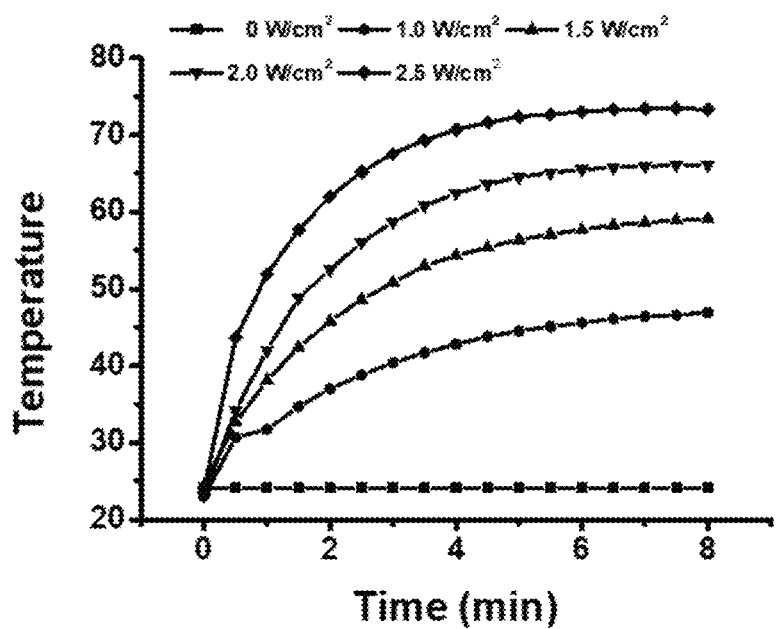
FIG. 2 shows temperature curves of the tumor photothermal therapy medicine ICG-II in the present disclosure, of the concentration of 10 μM at different power densities.
Figure 3:
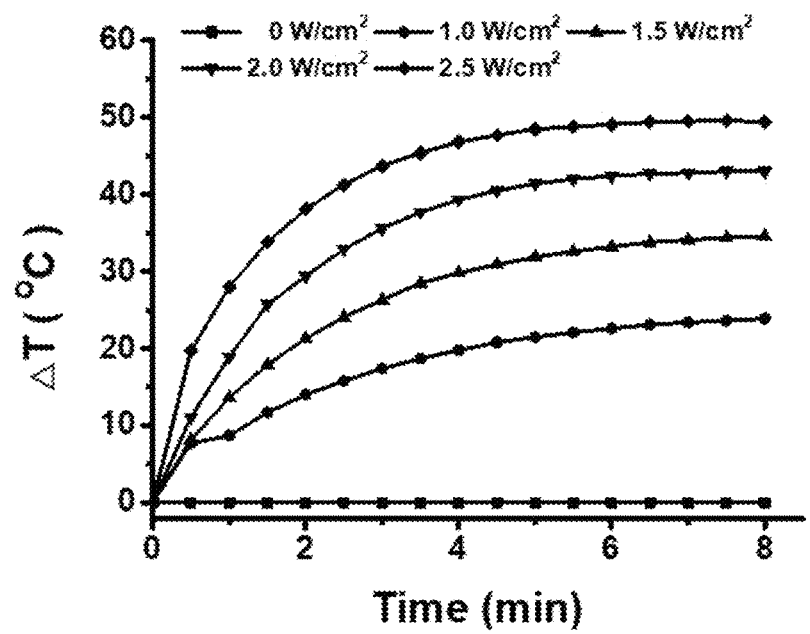
FIG. 3 shows temperature change curves of the tumor photothermal therapy medicine ICG-II in the present disclosure, of the concentration of 10 μM at different power densities.
Figure 4:
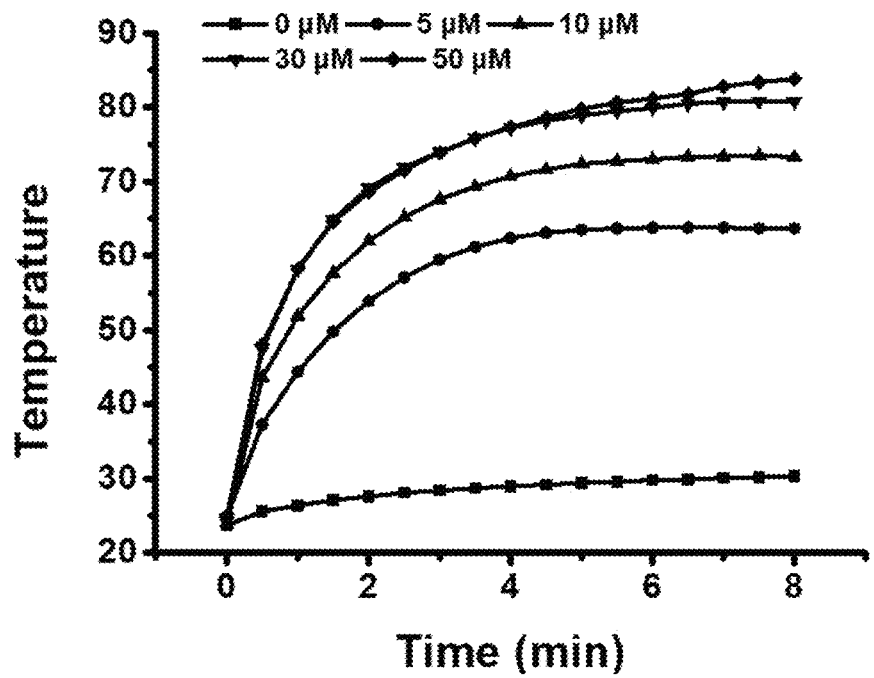
FIG. 4 shows temperature curves of the tumor photothermal therapy medicine ICG-II in the present disclosure, of different concentrations at a power density of 2.5 W/cm².
Figure 5:
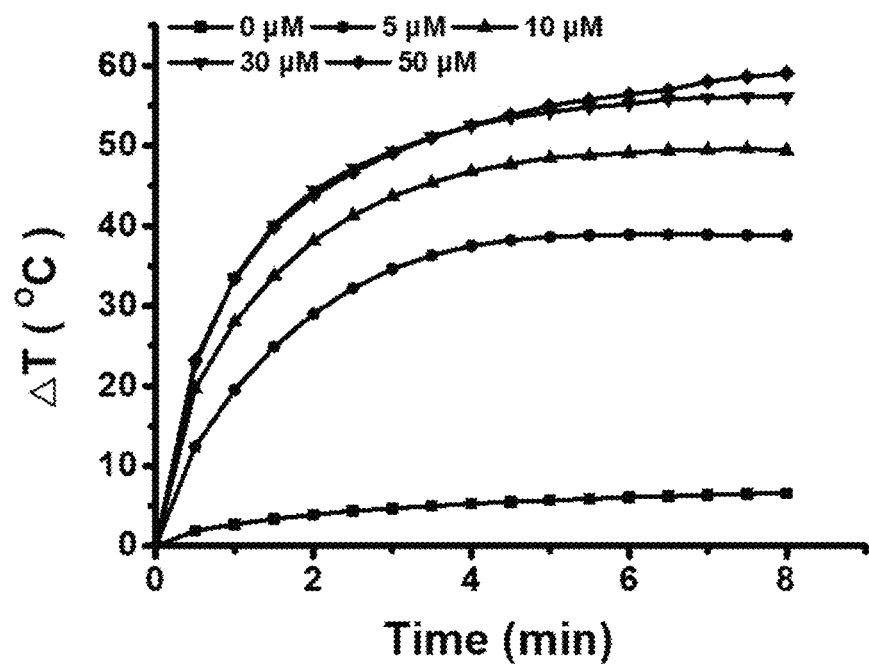
FIG. 5 shows temperature change curves of the tumor photothermal therapy medicine ICG-II in the present disclosure, of different concentrations at the power density of 2.5 W/cm².
Figure 6:
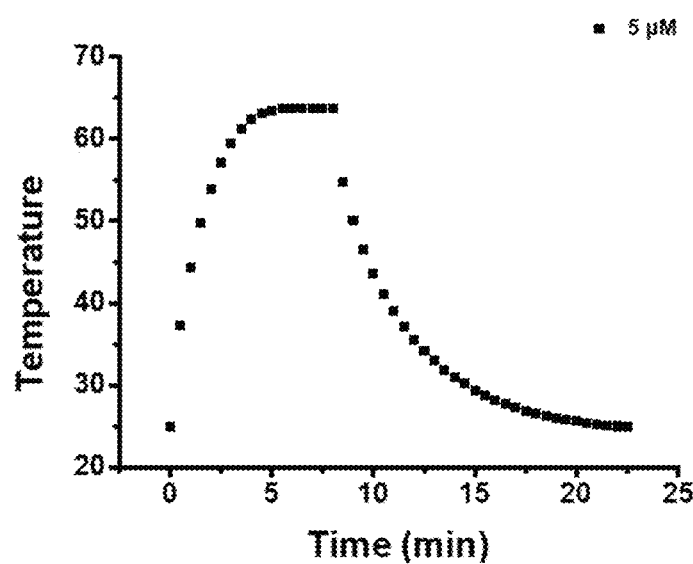
FIG. 6 shows photothermal effect of the ICG-II of a concentration of 5 μM at the power density of 2.5 W/cm², wherein light irradiation is stopped after 8 min.
Figure 7:
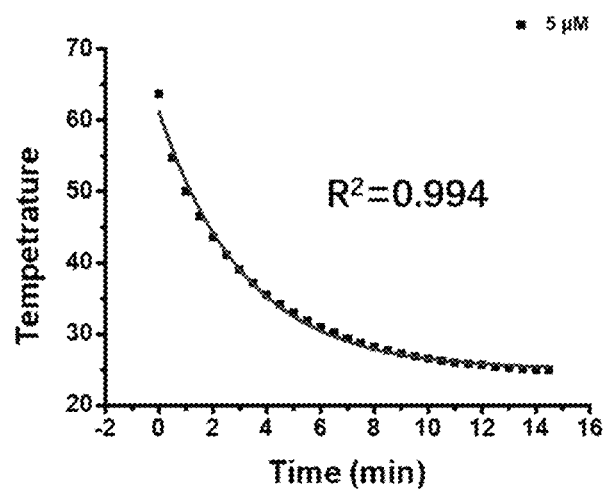
FIG. 7 shows a fitted curve of cooling time versus temperature of the ICG-II of the concentration of 5 μM at the power density of 2.5 W/cm² after irradiation.
Figure 8:
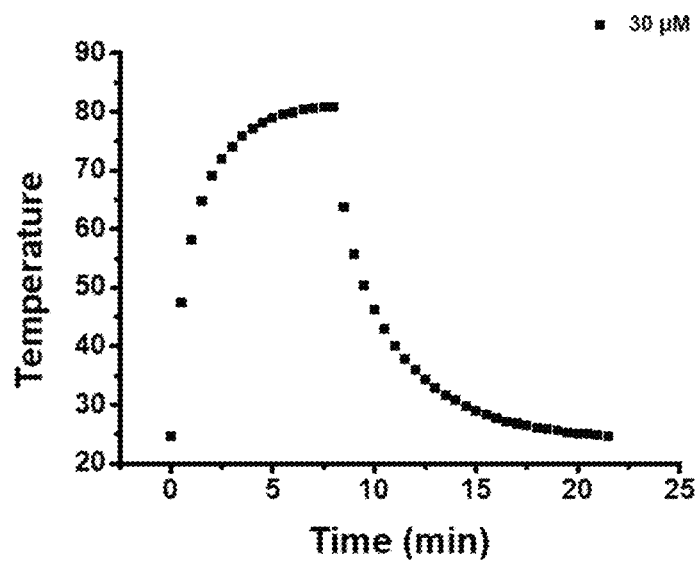
FIG. 8 shows photothermal effect of the ICG-II of a concentration of 30 μM at the power density of 2.5 W/cm², wherein light irradiation is stopped after 8 min.
Figure 9:
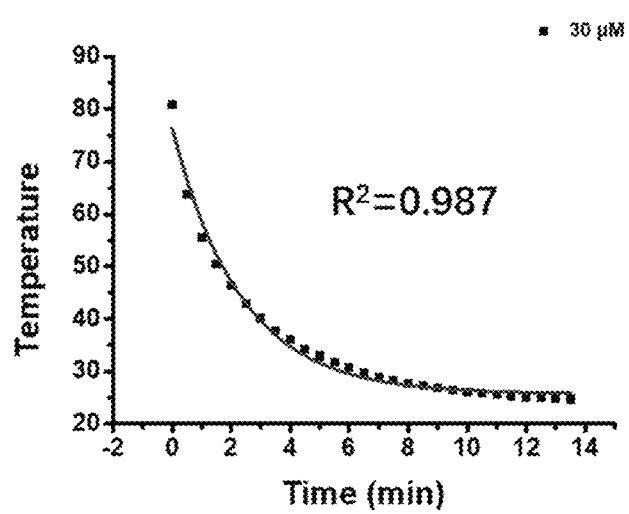
FIG. 9 shows a fitted curve of cooling time versus temperature of the ICG-II of the concentration of 30 μM at the power density of 2.5 W/cm² after irradiation.

Specific steps of the present disclosure are described below through examples, but are not limited by the examples.

The terms used in the present disclosure, unless otherwise indicated, generally have the meaning commonly understood by those of ordinary skill in the art.

The present disclosure is further described in detail below in combination with specific examples with reference to data. It should be understood that these examples are only intended to illustrate the present disclosure, but do not limit the scope of the present disclosure in any way.

EXAMPLE 1

1. Preparing an ICG-II solution of a concentration of 10 μM, and measuring temperature changes thereof at different powers;

Weighing a certain amount of ICG-II, dissolving the same in DMSO to prepare a mother liquor of a concentration of 1 mM, subsequently diluting the mother liquor with deionized water to prepare an experimental group solution of a concentration of 10 μM, adjusting, with a 785 nm laser device, a power density thereof to 1.0 W/cm², 1.5 W/cm², 2.0 W/cm², and 2.5 W/cm² respectively, measuring the temperature with a thermocouple thermometer under the condition of light irradiation at a time interval of 30 s, and turning off the laser device after the temperature reaching the highest temperature and being stable, and measuring cooling time thereof.

2. Preparing ICG-II of different concentrations, and measuring the temperature changes of the ICG-II of different concentrations at 2.5 W/cm²;

Weighing a certain amount of ICG-II, dissolving the same in DMSO to prepare a mother liquor of a concentration of 1 mM, subsequently diluting the mother liquor with deionized water to prepare experimental group solutions of four different concentrations 5 μM, 10 μM, 30 μM, and 50 μM, adjusting a power density thereof to 2.5 W/cm² with the 785 nm laser device, measuring the temperature with the thermocouple thermometer under the condition of light irradiation at a time interval of 30 s, and turning off the laser device after the temperature reaching the highest temperature and being stable, and measuring cooling time thereof.

3. Calculating photothermal conversion efficiency based on a photothermal conversion efficiency formula and performing comparison.

Based on the photothermal conversion efficiency formula, calculating a photothermal conversion efficiency, wherein the formula is as follows:

$$PTCE = \frac{hs(T_{max} - T_{surr}) - Q_{Dis}}{I(1 - 10^{-A})}$$

PTCE: photothermal conversion efficiency
h: heat transfer coefficient
s: container surface area
$Q_{Dis}$: heat dissipated by solvent and container
I: scattered power
A is the absorption at 785 nm $$hs = \frac{mC}{\tau_s}$$

m: mass of solution containing optical substances;
c: specific heat capacity
τs: correlation equation calculation $$t = -\tau_s \ln \theta$$

$$\theta = \frac{T - T_{surr}}{T_{max} - T_{surr}}$$

$$Q_{Dis} = hs(T'_{max} - T'_{surr})$$

T' refers to the temperature in water
The results of the measurement of the tumor photothermal therapy medicine ICG-II in the present disclosure, of different concentrations at a power density of 2.5 W/cm² are as shown in Table 1.

TABLE 1

| concentration | $\tau_s$ | hs | $T_{max}$ | $T_{surr}$ | ΔT | $Q_{Dis}$ | PTCE |
|---|---|---|---|---|---|---|---|
| 5 | 189.84 | 0.0055 | 63.8 | 24.9 | 38.9 | 0.0059 | 0.423 |
| 30 | 138.9 | 0.0076 | 80.8 | 24.7 | 56.1 | | 0.620 |
| 50 | 124.2 | 0.0085 | 84.9 | 24.9 | 60 | | 0.754 |

Figure 10:
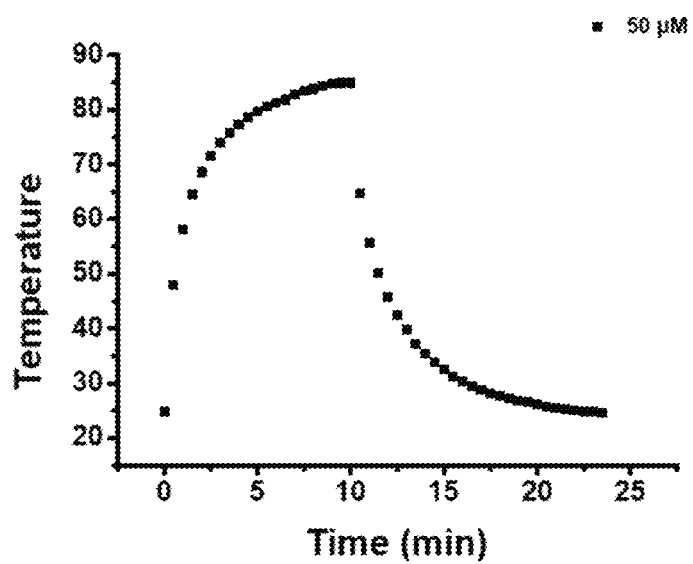
FIG. 10 shows photothermal effect of the ICG-II of a concentration of 50 μM at the power density of 2.5 W/cm², wherein light irradiation is stopped after 10 min.
Figure 11:
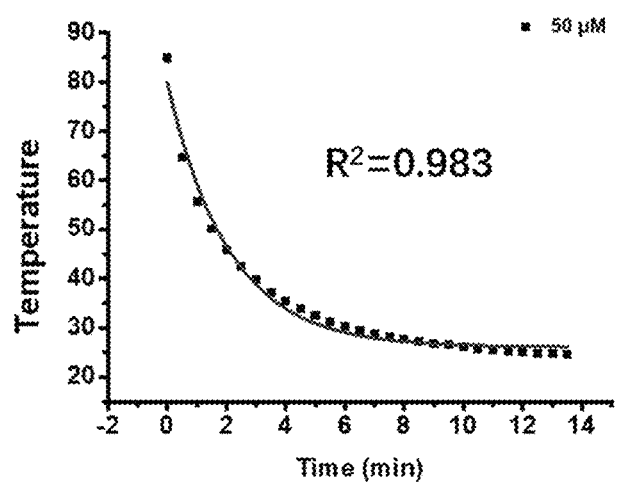
FIG. 11 shows a fitted curve of cooling time versus temperature of the ICG-II of the concentration of 50 μM at the power density of 2.5 W/cm² after irradiation.

Various data symbols in Table 1 represent the following meanings:
τs is a calculated value of the above photothermal formula
hs is a calculated value of the above photothermal formula
$T_{max}$ is a maximum temperature of thermocouple test within 5 min
$T_{sur}$ is an ambient temperature of initial test
ΔT is temperature difference between the maximum temperature and the initial temperature
$Q_{Dis}$: heat dissipated by solvent and container
PTCE is the photothermal conversion efficiency
FIG. 10 shows photothermal effect of the ICG-II of a concentration of 50 μM at the power density of 2.5 W/cm², wherein light irradiation is stopped after 10 min.
FIG. 11 shows a fitted curve of cooling time versus temperature of the ICG-II of a concentration of 50 μM at the power density of 2.5 W/cm² after irradiation, wherein a fitting parameter of the fitted curve is τs in the photothermal conversion efficiency calculation formula.
In the present disclosure, under a condition with 785 nm light irradiation at 2.5 W/cm², when the probe concentration is 50 μM, the photothermal conversion efficiency thereof is 75%, and the photothermal conversion efficiency is much higher than the photothermal conversion efficiency of indocyanine green ICG in the prior art, indicating that the present disclosure has the potential for efficient photothermal therapy.

EXAMPLE 2

1. The biotoxicity of the tumor therapeutic medicine ICG-II under a condition without light irradiation was studied through an MTT experiment by using HepG2 cancer cells and L02 normal cells.
HepG2 cell lines and L02 cell lines were selected as experimental cells, and MTT assay (3-(4,5-dimethylthiazol-2-yl)-2,5-diphenyltetrazolium bromide) was carried out according to standard protocols, so as to verify the biocompatibility of the probe.
Specifically, cells cultured/grown to an appropriate growth stage were added to a 96-well cell culture plate, and then incubated for 24 hours under a standard cell culture condition. ICG-II of different concentrations (0 μM, 5 μM, 10 μM, 30 μM, 50 μM, respectively) was co-cultured with the cells for 24 hours. Then each well was washed with PBS. 10 mL of MTT solution (of a concentration of 5 mg/ml) was added. After 4 hours of incubation, the culture medium containing the MTT solution was removed, DMSO (150 mL) was added to each well, and the cell culture plate was shaken on a shaker for 15 minutes to completely dissolve crystals. Finally, the absorbance of each well was measured at 490 nm with a plate reader. Since the absorption wavelength of the probe overlaps with the wavelength used in the MTT assay, a blank group will be set, and for the blank group, only the cells and the probe were used for incubation, while the MTT solution was not added, and other conditions were consistent with those of the experimental group. In the experiment, six repetition wells were set for each concentration, and cell viabilities were calculated.

Figure 12:
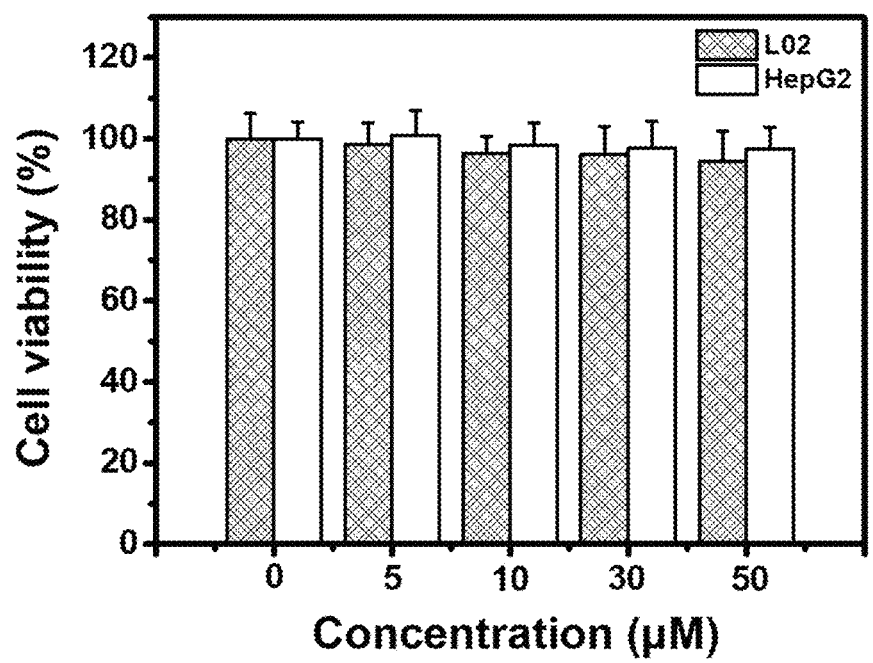
FIG. 12 shows a cytotoxicity assay of the tumor photothermal therapy medicine ICG-II in a condition without light irradiation.

A histogram was obtained by plotting the above cell viabilities, and was shown in FIG. 12. As shown in FIG. 12, under the condition without light irradiation, the small molecule compound probe ICG-II of the present disclosure shows no cytotoxicity in both HepG2 cancer cells and L02 cells, indicating that the small molecule compound probe ICG-II of the present disclosure has a very low toxic and side effect under the condition without light irradiation.

2. Under the condition of light irradiation at 1.5 W/cm$^2$, the cancer cell line HepG2 was irradiated, and the therapeutic effect of the tumor photothermal medicine was studied through MTT experiment.

HepG2 cell lines were selected as experimental cells, and MTT assay (3-(4,5-dimethylthiazol-2-yl)-2,5-diphenyltetrazolium bromide) was carried out according to standard protocols, so as to verify the photothermal treatment effect. Cells cultured/grown to an appropriate growth stage were added to a 96-well cell culture plate, and then incubated for 24 hours under a standard cell culture condition. ICG-II of different concentrations (0 μM, 5 μM, 10 μM, 30 μM, 50 μM, respectively) was co-cultured with the cells for 1 hour. Then irradiation was performed at 1.5 W/cm$^2$ for 5 min. A blank control group without light irradiation was additionally designed. Then each well was washed with PBS. 10 mL of MTT solution (of a concentration of 5 mg/ml) was added. After 4 hours of incubation, the culture medium containing the MTT solution was removed, DMSO (150 mL) was added to each well, and the cell culture plate was shaken on a shaker for 15 minutes to completely dissolve crystals. Finally, the absorbance of each well was measured at 490 nm with a plate reader. Since the absorption wavelength of the probe overlaps with the wavelength used in the MTT assay, a blank group will be set, and in the blank group, only the cells and the probe were used for incubation, while the MTT solution was not added, and other conditions were consistent with those of the experimental group. In the experiment, six repetition wells were set for each concentration, and cell viabilities were calculated.

Figure 13:
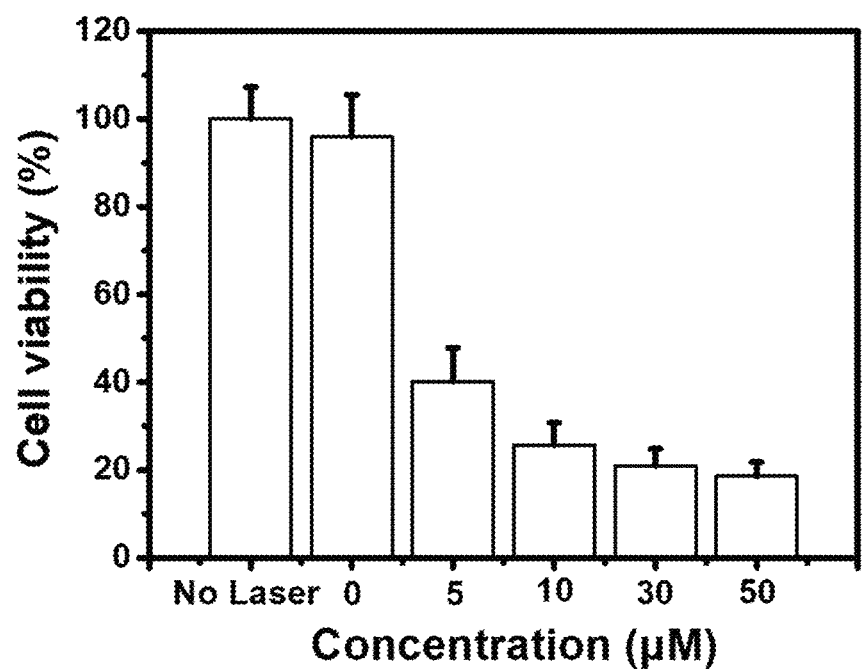
FIG. 13 shows a cytotoxicity assay of the tumor photothermal therapy medicine ICG-II at the power density of 2.5 W/cm².

A histogram was obtained by plotting the above cell viabilities, and was shown in FIG. 13. As shown in FIG. 13, under the condition with light irradiation, the small molecule compound probe ICG-II of the present disclosure shows a significant tumor cell killing ability in HepG2 cancer cells, and shows a dose dependency.

As shown in FIG. 13, when only the small molecule compound ICG-II of the present disclosure of a low concentration of 10 μM is used, the cell viability of cancer cells is reduced to about 25%; and when the small molecule compound ICG-II of the present disclosure of 50 μM is used, the cell viability of cancer cells is further reduced to 18.55%.

The above results fully prove that the small molecule compound ICG-II of the present disclosure has a powerful anti-tumor activity. The above experimental results fully prove that compared with the prior art, the small molecule compound probe ICG-II based on an indotricarbocyanine structure in the present disclosure has a significantly improved photothermal conversion efficiency, and the photothermal conversion efficiency is much higher than that of the indoletricyanine green ICG in the prior art, indicating that the small molecule compound probe ICG-II based on an indotricarbocyanine structure in the present disclosure has the potential for efficient photothermal therapy.

In addition, the small molecule compound probe ICG-II based on an indotricarbocyanine structure of the present disclosure shows a significant anti-tumor activity, and can be used as an effective medicine for photothermal therapy of tumors.

In addition, the small molecule compound ICG-II of the present disclosure shows no cytotoxicity under the condition without light irradiation; however, under the condition with light irradiation, the small molecule compound ICG-II of the present disclosure shows a significant anti-tumor activity. The properties of high activity and low toxic and side effects of the small molecule compound ICG-II of the present disclosure indicate that it will be widely applied in clinical practice.

The above are merely preferred examples of the present disclosure, rather than limiting the present disclosure, and any amendments, equivalent replacements, improvements and so on, made within the spirit and principle of the present disclosure, should be covered within the scope of protection of the present disclosure.

INDUSTRIAL APPLICABILITY

The present disclosure finds for the first time the photothermal use of the small molecule compound ICG-II based on an indotricarbocyanine structure. Compared with the indotricarbocyanine photothermal reagents in the prior art, the brand new small molecule compound ICG-II based on an indotricarbocyanine structure provided in the present disclosure has a significantly improved photothermal conversion efficiency, and the photothermal conversion efficiency can be up to 75%.

The present disclosure provides a small molecule probe based on an indotricarbocyanine structure efficient for tumor photothermal therapy. This small molecule probe has significant anti-tumor activity selective to light irradiation, and shows the properties of high activity and low toxic and side effects.

The small molecule probe based on an indotricarbocyanine structure provided in the present disclosure has excellent water solubility, has a high photothermal conversion efficiency in a small molecule state, does not need to be prepared into a nano material, avoids the defects of high biotoxicity and poor biological metabolism of nano materials, and has a wide clinical application prospect.

What is claimed is:

1. A method for photothermally treating a tumor, comprising injecting a therapeutically effective amount of a photothermal reagent to a to-be-treated area of a subject, and performing light irradiation on the to-be-treated area of the subject with a laser device at a power density, wherein the photothermal reagent is an indotricarbocyanine structure-based small molecule, and the indotricarbocyanine structure-based small molecule has a structural formula of:

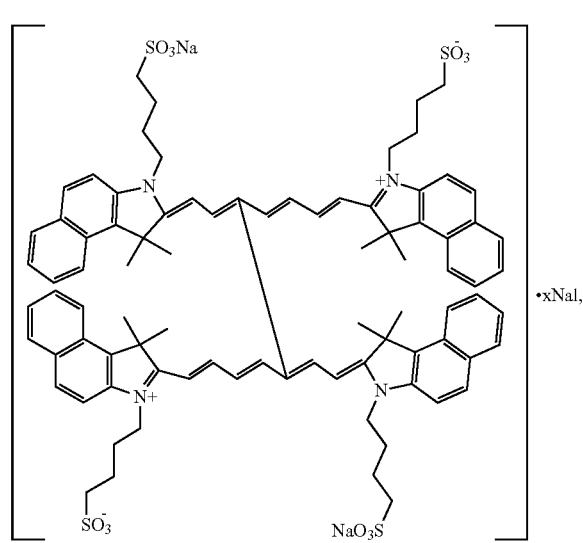

ICG-II

·xNaI, where x is greater than or equal to 1.

2. The method according to claim 1, wherein the power density is 1.0-2.5 W/cm$^2$.

3. The method according to claim 1, wherein the power density is 1.0 W/cm$^2$, 1.5 W/cm$^2$, 2.0 W/cm$^2$ or 2.5 W/cm$^2$.

4. The method according to claim 1, wherein a wavelength of the light irradiation is 785 nm.

5. The method according to claim 1, wherein the tumor is selected from the group consisting of liver cancer, retinoblastoma, lung cancer, leukemia, melanoma, pancreatic cancer, breast cancer, prostate cancer, ovarian cancer, bile duct cancer, bladder cancer, bone cancer, cervical cancer, colorectal cancer, esophageal cancer, gastric cancer, kidney cancer, laryngeal cancer, lymphoma, oral cancer, skin cancer, and thyroid cancer.

6. The method according to claim 2, wherein the power density is 1.0 W/cm$^2$, 1.5 W/cm$^2$, 2.0 W/cm$^2$ or 2.5 W/cm$^2$.

7. The method according to claim 2, wherein a wavelength of the light irradiation is 785 nm.

8. The method according to claim 3, wherein a wavelength of the light irradiation is 785 nm.

9. The method according to claim 2, wherein the tumor is selected from the group consisting of liver cancer, retinoblastoma, lung cancer, leukemia, melanoma, pancreatic cancer, breast cancer, prostate cancer, ovarian cancer, bile duct cancer, bladder cancer, bone cancer, cervical cancer, colorectal cancer, esophageal cancer, gastric cancer, kidney cancer, laryngeal cancer, lymphoma, oral cancer, skin cancer, and thyroid cancer.

10. The method according to claim 3, wherein the tumor is selected from the group consisting of liver cancer, retinoblastoma, lung cancer, leukemia, melanoma, pancreatic cancer, breast cancer, prostate cancer, ovarian cancer, bile duct cancer, bladder cancer, bone cancer, cervical cancer, colorectal cancer, esophageal cancer, gastric cancer, kidney cancer, laryngeal cancer, lymphoma, oral cancer, skin cancer, and thyroid cancer.

11. The method according to claim 4, wherein the tumor is selected from the group consisting of liver cancer, retinoblastoma, lung cancer, leukemia, melanoma, pancreatic cancer, breast cancer, prostate cancer, ovarian cancer, bile duct cancer, bladder cancer, bone cancer, cervical cancer, colorectal cancer, esophageal cancer, gastric cancer, kidney cancer, laryngeal cancer, lymphoma, oral cancer, skin cancer, and thyroid cancer.

* * * * *